(12) United States Patent
Mendell

(10) Patent No.: US 6,237,603 B1
(45) Date of Patent: May 29, 2001

(54) METHOD AND SYSTEM FOR REVERSING PHYSIOLOGICAL CHANGES IN HUMAN BEINGS USING ACUPUNCTURE AND HYPNOSIS

(76) Inventor: Sherwin Mendell, 5200 SW. 18th St., Plantation, FL (US) 33317

( * ) Notice: Subject to any disclaimer, the term of this patent is extended or adjusted under 35 U.S.C. 154(b) by 0 days.

(21) Appl. No.: 07/995,683

(22) Filed: Dec. 23, 1992

(51) Int. Cl.[7] .............................. A61B 19/00; A61B 17/00
(52) U.S. Cl. ........................ 128/897; 128/907; 606/189; 606/204
(58) Field of Search .................. 128/897–99, 907; 606/189, 204

(56) References Cited

U.S. PATENT DOCUMENTS

| | | |
|---|---|---|
| 3,908,634 | 9/1975 | Mongahan . |
| 4,073,296 | 2/1978 | McCall . |
| 4,098,277 | 7/1978 | Mendell . |
| 4,157,088 | 6/1979 | Gracey . |
| 4,227,516 | 10/1980 | Meland et al. . |
| 4,282,864 | 8/1981 | Pizer . |
| 4,450,846 | 5/1984 | McCall . |
| 4,895,149 | 1/1990 | Moren . |
| 4,966,164 | * 10/1990 | Colsen et al. ............... 128/907 |
| 5,024,650 | 6/1991 | Hagiwara . |
| 5,054,486 | 10/1991 | Yamada . |
| 5,211,184 | * 5/1993 | Yee et al. .................. 128/907 |

FOREIGN PATENT DOCUMENTS

| | | |
|---|---|---|
| 1022708A | 9/1981 | (SU) . |
| 1022708 | * 6/1983 | (SU) ......................... 128/907 |

* cited by examiner

Primary Examiner—John P. Lacyk
(74) Attorney, Agent, or Firm—Malin, Haley & DiMaggio, P.A.

(57) ABSTRACT

A method and apparatus for reversal of physiological human dependency that can be induced by nicotine, alcohol, or drugs, for example, and for reducing or eliminating dependency through the use of acupuncture simultaneously with hypnosis. The invention also includes a kit that allows for self-administration of both acupuncture and self-induced hypnosis by the patient for intensifying and accelerating the effects of both the acupuncture and the hypnosis in reversing chemical physiological and psychotherapeutic addiction, pain, mental and/or physiologic health problems in human beings.

5 Claims, 1 Drawing Sheet

FIGURE
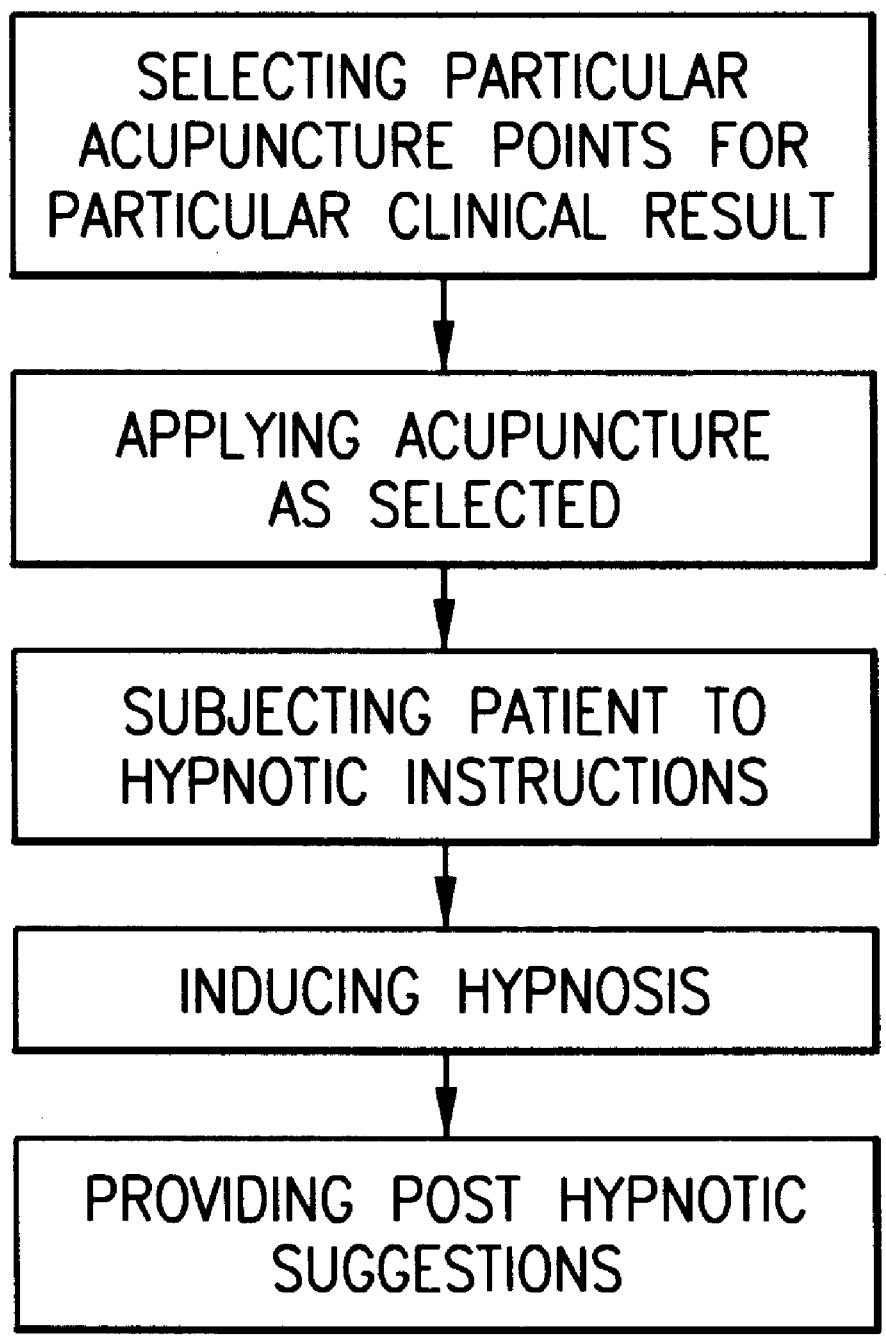

METHOD AND SYSTEM FOR REVERSING PHYSIOLOGICAL CHANGES IN HUMAN BEINGS USING ACUPUNCTURE AND HYPNOSIS

BACKGROUND OF THE INVENTION

1. Field of the Invention

This invention relates to a method and apparatus that provides for reversal of physiological human dependency induced by cigarette smoking, alcohol or drug addiction, for reducing or eliminating physiological dependency through the use of acupuncture and psychological changes through hypnosis, employing tapes, records or compact disks, and in particular, to a method and self-administering patient kit that utilizes specific acupuncture/acupressure locations in combination with hypnosis which intensifies and accelerates the effects of acupuncture/acupressure in reversing chemical, physiological and psychotherapeutic addiction in human beings induced by cigarette smoking, and in particular nicotine, alcohol addiction and drug addiction. The method and apparatus may also be used for weight loss, areas of self-improvement such as memory, relief from stress (relaxation), control of physiologic and/or psychological pain, and the like.

2. Description of the Prior Art

Acupuncture/acupressure, as a Chinese remedy for medical and psychophysiological problems such as addiction, are well known in the art. For the sake of this application, acupuncture and acupressure are to be considered synonymous. Acupuncture has been used to treat a variety of human physical and psychological problems. Different forms of acupuncture that include tactile stimulation of various areas of the body, either through pressure, electrical stimulation or magnetic stimulation are known. Numerous types of acupuncture devices are known, such as that shown in U.S. Pat. No. 4,450,846 for an electrical pulse acupuncture apparatus. U.S. Pat. No. 4,966,164 shows a combined sound generating device, an electrical acupuncture method and device that attaches to portions of the human body for treatment.

Hypnosis has been used for treatment of dependency in human beings for smoking, alcohol and drug addiction. The purpose of hypnosis is to provide for post-hypnotic suggestion which is effective with particular individuals for both physiological and psychological treatment of chemical dependency. U.S. Pat. No. 4,282,864 shows a method and apparatus for inducing a pre-hypnotic state to enhance suggestion.

Although acupuncture in and of itself may, at times, produce successful results for both physiological and psychological treatments, and hypnosis has been used by itself for improving psychological and physiological treatment of dependency, Applicant has discovered that the simultaneous use of hypnosis in conjunction with stimulation of particular acupuncture zones greatly intensifies and amplifies the acupuncture effect, with a result greater than any individual effect noted heretofore by the Applicant, especially for treatment of cigarette smoking, alcohol addiction and drug addiction, to greatly reverse chemical changes through the application of this treatment. The system may be utilized in the form of a self-administered patient kit that includes a device for applying acupressure or acupuncture pressure at prescribed and preselected points on a human being's skin that is used in conjunction with audio instructions on a cassette tape, compact disk, or record that will induce hypnosis in a predetermined schedule. The kit includes a body point chart with the instructions. An instruction sheet or cassette could also be in the kit explaining how to do self-hypnosis. The tape provided could be subliminal or with audio conscious levels or both. Applicant is the patentee of U.S. Pat. No. 4,098,277, which provides for stimulating auricular acupuncture points which would be used in conjunction with hypnosis in the present invention.

SUMMARY OF THE INVENTION

A method and apparatus for treating addiction or other psychophysiological or physiological problems in human beings, to provide for a reversal of certain physiological changes caused by smoking (nicotine addiction), alcohol, or drug addiction through the simultaneous application of acupuncture treatment and hypnosis, which aids in amplifying and intensifying the effect of acupuncture on the patient. The apparatus may include a device for stimulating particular predetermined acupuncture points on the human skin, mechanically, electrically, or magnetically, a device for inducing heterohypnosis, such as audio instruction on a cassette tape, record, or compact disk, body point charts with instructions for the acupuncture (acupressure) stimulation, and instructions for self-use of both the acupuncture device and the cassette tape that induces hypnosis, and instructions for self-hypnosis.

As an example, the patient can use specifically the device shown by Applicant in U.S. Pat. No. 4,098,277, which includes a method for selectively applying pressure to discreet selected auricular acupuncture pressure points, but without penetrating the skin. Once the device is made, which has predetermined pressure points for mounting on a human being such as in the ear area, such a device could be included in the kit.

Many acupuncture points for treating a wide variety of disorders are located in accordance with known acupuncture text, such as Czaplicki on pages 134–137. Once the particular points are know, either an attachable device or magnetic wand/pointer is used that can apply stimulus to these acupuncture points. Also, needles may be used. In accordance with the present invention, the patient would apply the acupuncture pressures to particular points on the human body for solving a specific disorder. Next, the patient would undergo self-hypnosis by listening to the instructions on the recording or cassette tape. The patient would also receive a post-hypnotic suggestion, which is also provided for in conjunction with the stimulation by acupuncture. Applicant has found that simultaneous hypnosis greatly intensifies and amplifies the positive effects of acupuncture and vice versa.

Although shown in kit form, broadly the method may be utilized which combines recorded heterohypnosis or self-hypnosis techniques and acupuncture to specifically treat particular types of physiological, psychological, or psychophysiological disorders through the treatment described herein.

It is an object of this invention to provide an improved method technique and treatment, particularly for eliminating smoking, alcohol addiction, drug addiction or weight loss that combines the use of acupuncture for predetermined treatment of illnesses in specific zone locations while simultaneously having the patient subject to hypnosis, which acts to intensify and amplify the effects of the acupuncture.

It is another object of this invention to provide a patient kit which may be utilized by a patient that contains acupuncture body point charts with instructions, a device or devices to apply the acupuncture pressure, and a device for inducing hypnosis and applying hypnosis to the individual patient, such as audio instructions in a cassette tape, compact disk, or record or written instructions. The kit frees the patient from the need to be hospitalized or return to the therapist's office for regular treatment.

And yet still another object of this invention is to provide a method and apparatus for amplifying and accelerating the effects of acupuncture through hypnosis.

In accordance with these and other objects which will be apparent hereinafter, the instant invention will now become described with particular reference to the accompanying drawings.

BRIEF DESCRIPTION OF THE DRAWINGS

The FIGURE shows the overall step-by-step process in a flow chart to utilize the present invention.

DESCRIPTION OF THE PREFERRED EMBODIMENTS

A method and apparatus for reversal of physiological and/or psychological human dependency induced by nicotine addiction, alcohol, or drug addiction, utilizing known techniques in acupuncture in conjunction and simultaneously while applying acupuncture, using hypnosis, whether self-induced or induced by a professional trained hypnotist live or by a recording.

Referring now to the FIGURE, the method is shown in the preferred embodiment for reversing the dependency of nicotine, alcohol, or drug addiction.

The first step involves selecting particular acupuncture points to provide a particular clinical result. For example, if nicotine addiction is to be reversed, particular acupuncture points will be determined through the literature and selected for maximum effective results. Once these particular location points on the human body have been determined for the specific clinical result sought, the next step is applying the acupuncture itself as selected. In the preferred embodiment, acupuncture needles can be used or a mechanical device that provides specific mechanical pressure tactilely to the skin of a human being at the exact acupuncture points desired for treatment. A specific physical structure is shown in U.S. Pat. No. 4,098,277 which is incorporated herein. Other acupoint stimulating devices could be employed such as magnets, ball bearings attached to adhesive, piezo or other electrical devices, or laser.

Once the acupuncture treatment has begun and is continuing, the patient is then subjected to hypnotic suggestions and instructions in order to induce a hypnotic state. Hypnosis herein means an altered state of human consciousness (often trance-like). This can be done by a trained professional hypnotist or through self-hypnotic instructions. In the preferred embodiment for self-hypnosis, an audio tape is presented which is turned on by the patient and listened to in order to induce hypnosis in the patient. The audio affirmations, suggestions, and information also will provide post-hypnotic suggestions for reinforcing psychologically the information needed and given in the hypnotic state to reverse the desired addiction.

Therefore, during the acupuncture treatment, the patient will have induced hypnosis. The information will provide further audio messages that allow for eliminating psychological dependency of a particular addiction such as nicotine, alcohol, or drugs such as auto suggestion in the non-hypnotic state. In addition, there will be other information regarding the posthypnotic suggestions discussed for the particular clinical result.

From a hardware standpoint, the invention can be provided as an apparatus in kit form that would include a physical device for applying acupuncture pressure such as that specifically shown in Applicant's U.S. Pat. No. 4,098,277 which includes a device for applying pressure points to the skin. The kit would also include an audio cassette tape that has the full instructions for inducing hypnosis and/or teaching self-hypnosis and provides all the necessary additional information that is utilized when the patient is under hypnosis for eliminating the addiction in the patient. The audio tape will also include post-hypnotic suggestions for helping reinforce the message to reverse the addiction in the patient. The audio cassette could also be a compact disk or record or any other type of medium that provides an audio message in known technology today. Instructions could also be given on a computer screen or video cassette or written on an instruction sheet.

EXAMPLE 1

A twenty-one year old male was selected that was a heavy user of marijuana. Based on the subject's statement, the subject had used marijuana for ten years of his twenty-one years and in the last six years, marijuana was used heavily. The subject was treated three sessions for approximately forty minutes per session, which consisted of a combination of hypnosis with background sounds such as music, nature sounds, ocean waves, running brook water, and subliminal suggestions for eliminating psychological urges and cravings. Hypnosis cassette tapes were given to the subject for home use. The subject was taught self-hypnosis and provided also with printed instructions. Acupressure points that are known in the literature were used on the patient's ears, arms, face, legs, and body at each session simultaneously with the hypnosis. No needles were used for the acupuncture application. The points were stimulated with various piezo electric shock, ruby laser, pressure ACU-patch, which is a small ball bearing attached to the skin with a piece of tape. The patient stopped smoking marijuana.

EXAMPLE 2

The subject was a male, Caucasian, age fifty-six. The subject had a history of being a heavy user of alcohol and in particular, beer. The subject had consumed about twelve cans of beer daily. It was the subject's desire to get consumption under control, not necessarily stop. The subject also has been smoking one and one-half packs of cigarettes per day for forty-three years.

The subject, within three days, had completely stopped smoking and by choice has had only three cans of beer in two weeks. The subject claims that he can easily walk away without any additional urges for alcohol. The treatment plan used was the same as that employed in Example 1. Essentially, the subject was treated for approximately forty minutes at an office visit that consisted of a combination of hypnosis with background sounds such as music, nature, ocean waves. Acupuncture points that were known in the field and in the literature for this type of clinical treatment were used on the ears, arms, face, legs, and body at each session, simultaneously along with hypnosis.

EXAMPLE 3

The patient is a white male, age forty-eight, with a pinched nerve, some arthritis on the hip, and a birth defect of spina bifida. The patient was unable to walk without support or even stand without support. The patient experienced severe, non-stop, throbbing pain. The patient has been seeing an orthopedic surgeon and a chiropractor for a month and his condition was not improving or getting worse. After one treatment, pain was reduced by approximately forty percent. The treatment was the combination of acupuncture and hypnosis. The patient was subjected to three sessions in accordance with the process described in Example 1 herein in a six day period. The patient felt that there was approximately an eighty percent improvement in the pain reduction.

In applying the methodology in accordance with the Examples above and other studies performed by Applicant, the crux is that known methods of acupuncture for specific clinical treatments can be combined with hypnosis, whether induced by a professional or even with self-induced hypnosis using audio tapes, compact disks, or records to achieve the desired results or learning self-hypnotic techniques.

It is impossible to separate physiological and psychological disorders. As an example, a fractured finger would affect a typist, simultaneously causing physiological, psychological, or psychophysiological trauma. The fracture must heal physiologically. "Will I be able to use my finger to type as before?" (psychological effect). Thus, a purpose for the invention is to treat physiological and psychological (psychophysiological) disorders.

With respect to the acupuncture itself, the traditional acupuncture using needles can be used or acupressure without needles that apply pressure with various stimuli such as piezo electric shock, ruby laser pressure, ACU-patch, which is a small ball bearing attached to the skin with adhesive tape. Also a tei-shin modulator cutaneous spring-loaded probe that applies pressure without puncturing due to rounded tips can be used.

In the kit form, hetero and self-induced hypnosis is envisioned. Thus, the kit would include hardware and instructions to provide the acupuncture stimulus and written and audio instructions for inducing hypnosis and post-hypnotic suggestions.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method for reversing physiological human dependency induced by nicotine, alcohol, or other drugs, comprising the steps of:
   (a) selecting particular acupressure points on a patient to obtain the particular clinical results;
   (b) applying acupressure in accordance with the selected particular points for a particular clinical result;
   (c) simultaneously subjecting the patient to hypnotic instructions to induce hypnosis;
   (d) inducing hypnosis in the patient;
   (e) providing the patient while under hypnosis certain psychological suggestions for relieving dependency;
   (f) terminating the trance state of hypnosis on the patient; and
   (g) terminating the acupressure.

2. An apparatus for reversing psychological human dependency induced by nicotine, alcohol, or other drugs comprising:
   means for applying acupressure to a patient in accordance with predetermined body areas for reducing psychological human dependency; and
   means used with said acupressure means for inducing hypnosis through audio stimuli to said patient while said patient is being treated with acupressure to reverse human physiological dependency based on cigarette smoking, alcohol, or drug addiction.

3. An apparatus as in claim 2, including:
   audio means for storing and broadcasting specific instructions for self-hypnosis for use in conjunction with acupressure for reducing human physiological dependency.

4. A system for the self-administration of hypnosis and acupressure on one's person for eliminating chemical dependency comprising:
   a tape means for storing audio and video instructions and sounds to induce self-administered hypnosis to a subject;
   a pressure inducement bar oblong in shape with at least one blunt end for allowing the subject to apply self-administered pressure to their body at selective areas; and
   an acupressure chart for indicating to the subject selective areas of the human body where acupressure should be applied.

5. A method to reduce compulsive disorders such as overeating, comprising the steps of:
   self-inducing hypnosis on ones person by listening to taped instructions and sounds;
   observing a pictorial chart to determine specific body locations in which to apply self-administered acupressure;
   applying self-administered acupressure to said specific body points;
   suggesting to the subject through the use of said taped instructions, while in a hypnotic state, to reduce and cease said compulsive disorder;
   terminating the self-induced hypnosis; and
   terminating the self-administered acupressure.

* * * * *